US009486243B2

United States Patent
Eskuri

(10) Patent No.: US 9,486,243 B2
(45) Date of Patent: Nov. 8, 2016

(54) SYSTEMS AND METHODS FOR TREATMENT OF PREMENSTRUAL DYSPHORIC DISORDERS

(71) Applicant: Covidien LP, Mansfield, MA (US)

(72) Inventor: Alan D. Eskuri, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 157 days.

(21) Appl. No.: 13/654,235

(22) Filed: Oct. 17, 2012

(65) Prior Publication Data
US 2013/0116677 A1 May 9, 2013

Related U.S. Application Data

(60) Provisional application No. 61/556,935, filed on Nov. 8, 2011.

(51) Int. Cl.
*A61B 17/28* (2006.01)
*A61B 17/42* (2006.01)
(Continued)

(52) U.S. Cl.
CPC ........... *A61B 17/42* (2013.01); *A61B 18/1445* (2013.01); *A61B 18/1815* (2013.01); *A61B 2017/4216* (2013.01); *A61B 2018/00434* (2013.01); *A61B 2018/00559* (2013.01); *A61B 2018/00791* (2013.01); *A61B 2018/00839* (2013.01); *A61B 2018/00875* (2013.01); *A61N 7/02* (2013.01)

(58) Field of Classification Search
CPC .......... A61B 2018/00559; A61B 2018/00434; A61B 18/1445; A61B 18/1815; A61B 2017/4216; A61B 2018/0055; A61B 17/29; A61B 2018/00607; A61B 2018/1455; A61B 18/1442; A61B 17/176; A61B 17/282; A61B 17/42; A61B 18/085; A61N 1/36021; A61C 5/026
USPC ..................................... 606/21–52
See application file for complete search history.

(56) References Cited

U.S. PATENT DOCUMENTS

| 4,014,988 A | 3/1977 | Pharriss et al. |
| 4,016,270 A | 4/1977 | Pharriss et al. |

(Continued)

FOREIGN PATENT DOCUMENTS

| WO | 2006/042117 A2 | 4/2006 |
| WO | 2007/006158 A1 | 1/2007 |
| WO | 2008/003058 A2 | 1/2008 |

OTHER PUBLICATIONS

M. Carr, "Selections from Current Literature Treatments for premenstrual dysphoric disorder" Family Practice 2001; vol. 18 No. 6 pp. 644-646.

(Continued)

*Primary Examiner* — Ronald D Hupczey, Jr.
*Assistant Examiner* — Yasamin Ekrami

(57) ABSTRACT

An endoscopic procedure for the parasympathetic and sympathetic denervation of the nerves of the ovaries and uterus for management of endocrine dysphoric disorders. The tissues of selected inferior mesenteric and pelvic nerves are heated via introduction of radiofrequency energy at sufficient power and time to induce complete or partial nerve blockade while leaving the supporting tissue structurally intact. In some embodiments, the suspensory ligament of the ovary, the ovarian ligament, and/or the uterosacral ligament are heated to a range of 45° C. to 65° C. for a period of about 5 seconds to about 60 seconds.

14 Claims, 5 Drawing Sheets

(51) Int. Cl.
*A61B 18/14* (2006.01)
*A61B 18/00* (2006.01)
*A61N 7/02* (2006.01)
*A61B 18/18* (2006.01)

(56) References Cited

U.S. PATENT DOCUMENTS

| | | | |
|---|---|---|---|
| 4,949,718 A * | 8/1990 | Neuwirth et al. | 607/27 |
| 5,188,122 A | 2/1993 | Phipps et al. | |
| 5,433,739 A | 7/1995 | Sluijter et al. | |
| 5,558,672 A | 9/1996 | Edwards et al. | |
| 5,569,241 A | 10/1996 | Edwards | |
| 5,571,147 A | 11/1996 | Sluijter et al. | |
| 5,658,322 A | 8/1997 | Fleming | |
| 5,964,755 A | 10/1999 | Edwards | |
| 6,002,968 A * | 12/1999 | Edwards | 607/101 |
| 6,006,755 A * | 12/1999 | Edwards | 128/898 |
| 6,026,331 A | 2/2000 | Feldberg et al. | |
| 6,122,549 A | 9/2000 | Sharkey et al. | |
| 6,146,380 A | 11/2000 | Racz et al. | |
| 6,159,207 A * | 12/2000 | Yoon | A61B 19/40 606/41 |
| 6,161,048 A | 12/2000 | Sluijter et al. | |
| 6,259,952 B1 * | 7/2001 | Sluijter et al. | 607/100 |
| 6,546,933 B1 * | 4/2003 | Yoon | 128/898 |
| 6,565,561 B1 * | 5/2003 | Goble et al. | 606/41 |
| 6,669,691 B1 | 12/2003 | Taimisto | |
| 6,725,095 B2 | 4/2004 | Fenn et al. | |
| 7,258,688 B1 | 8/2007 | Shah et al. | |
| 7,258,690 B2 | 8/2007 | Sutton et al. | |
| 7,309,336 B2 | 12/2007 | Ashley et al. | |
| RE40,279 E * | 4/2008 | Sluijter et al. | 607/100 |
| 7,425,212 B1 | 9/2008 | Danek et al. | |
| 7,452,358 B2 * | 11/2008 | Stern et al. | 606/41 |
| 7,771,357 B2 | 8/2010 | Burbank et al. | |
| 8,419,727 B2 * | 4/2013 | Koss et al. | 606/34 |
| 2004/0215182 A1 * | 10/2004 | Lee | 606/32 |
| 2006/0079874 A1 * | 4/2006 | Faller et al. | 606/40 |
| 2006/0259034 A1 * | 11/2006 | Eder et al. | 606/50 |
| 2007/0265613 A1 * | 11/2007 | Edelstein et al. | 606/37 |
| 2008/0015664 A1 | 1/2008 | Podhajsky | |
| 2008/0039835 A1 * | 2/2008 | Johnson et al. | 606/48 |
| 2008/0161874 A1 * | 7/2008 | Bennett et al. | 607/39 |
| 2009/0054887 A1 | 2/2009 | Podhajsky | |
| 2009/0076409 A1 | 3/2009 | Wu et al. | |
| 2009/0187232 A1 * | 7/2009 | Salim | 607/46 |
| 2010/0114086 A1 | 5/2010 | Deem et al. | |
| 2010/0168731 A1 * | 7/2010 | Wu et al. | 606/33 |
| 2011/0213448 A1 * | 9/2011 | Kim | 607/133 |
| 2011/0308527 A1 * | 12/2011 | Harrington et al. | 128/831 |

OTHER PUBLICATIONS

Casper et al., "The effect of hysterectomy and bilateral oophorectomy in women with severe premenstrual syndrome" American Journal Obstetrics Gynecology; Jan. 1990; vol. 162, No. 1, pp. 105-109.
Instruction Manual for LigaSure LF 1537; Aug. 2009; Covidien AG.

* cited by examiner

SYSTEMS AND METHODS FOR TREATMENT OF PREMENSTRUAL DYSPHORIC DISORDERS

CROSS-REFERENCE TO RELATED APPLICATION

This application claims the benefit of and priority to U.S. Provisional Application Ser. No. 61/556,935 entitled "OVARIAN DENERVATION", filed Nov. 8, 2011 by Alan David Eskurl, the entirety of which is incorporated by reference herein for all purposes.

BACKGROUND

1. Technical Field

The present disclosure generally relates to endoscopic general surgery, and more particularly, to surgical systems, devices, and methods for electrosurgical denervation and endocrine management of the female reproductive organs.

2. Background of Related Art

Electrosurgery is a technique of using alternating current electrical signals, using a carrier frequency in the approximately 200 kHz-3.3 mHz range, in connection with surgical instruments, to cut or coagulate biologic tissue endogenically. This electrosurgical signal can be a sinusoidal waveform operating in a continuous mode at a 100% duty cycle, or pulse modulated at a duty cycle of less than 100%. Typically, electrosurgical signals are operated at 100% duty cycle for maximal cutting effect, and are pulse modulated at duty cycles ranging from 50% to 25% for less aggressive cutting, also referred to as blending, or, at a substantially lower duty cycle of approximately 6%, for coagulating.

The electrosurgical carrier signal can be varied in intensity, and manner of application. Electrosurgical energy may be applied to a patient via electrodes in either a monopolar mode, or a bipolar mode. In monopolar mode, an active electrode is provided by the surgical instrument at the surgical site and a return electrode is positioned elsewhere on the patient (typically buttocks or thigh), such that the electrosurgical signal passes through the patient's body from the surgical site to the return electrode. In bipolar mode, both the active and return electrodes are provided by the instrument positioned at the surgical site and may be effectuated by, for example, both tines of a pair of forceps. In bipolar procedures, the electrosurgical signal passes through the tissue that is held between the electrodes of the instrument. A surgeon's decision to use monopolar or bipolar mode electrosurgery is often based upon various factors, including for example the type of procedure to be performed, or whether the patient is fitted with a metallic prosthesis or cardiac pacemaker.

Premenstrual dysphoric disorder (PMDD) is a severe form of premenstrual syndrome (PMS) that may be diagnosed by observing a pattern of symptoms. According to a report by the Committee on Gynecologic Practice of the American College of Obstetricians and Gynecologists, up to eighty percent of women of reproductive age experience physical changes related to menstruation. Twenty to forty percent of such women experience symptoms of PMS, while two to ten percent report that menstruation causes severe disruption of their daily activities. Menstruation-related physical discomfort, such as dysmenorrhea, may begin with a woman's first menstrual cycle (menarche). Often, this condition is superseded by PMS in late adolescence or by a woman's early twenties. These syndromes generally remain stable over time.

The serotoninergic antidepressants are a first-line treatment for severe PMDD. For example, a daily 20 mg dose of Fluoxetine has been shown to be superior to placebo, whether used only during the post-ovulation (luteal) phase or throughout the full menstrual cycle.

It has been shown that by inducing anovulation and amenorrhea, the use of GnRH agonists, leuprolide, histrelin, and/or goserelin provide significant relief of symptoms in patients without comorbid depression. However, these medications can induce menopausal symptoms such as hot flushes, vaginal dryness, fatigue, irritability, cardiac problems, and osteopenia. In women with a history of PMDD, treatment of induced menopause with estrogen, or with estrogen in combination with progestational agents, can induce recurrent symptoms of PMDD. This finding supports the theory that female gonadal hormones have an etiologic role in PMDD.

In very rare cases of severe PMDD, surgical ovarian removal (oophorectomy) may be considered, because ovary removal has been shown to relieve PMDD symptoms. Endoscopic surgery for the ligation of fallopian tubes and other bodily vessels with the use of radiofrequency energy is well known to the field of gynecology. Such instruments effect sealing of bodily vessels via the application of electrosurgical energy to tissue and are used in resection procedures. In addition, the use of radiofrequency energy for denervation of adrenergic organs, such as the kidneys, is known to the medical art.

SUMMARY

The present disclosure relates to an electrosurgical apparatus and methods for electrosurgically denervating the sympathetic and parasympathetic nerves of the ovaries and uterus, such as, without limitation, nerves of the suspensory ligament of the ovary, nerves of the ovarian ligament, and/or nerves of the uterosacral ligament.

In one aspect of the present disclosure, an endoscopic device and method of use thereof for delivering radiofrequency energy to the inferior mesenteric and pelvic nerve for endocrine management of the female reproductive organs is presented. In some embodiments, an endoscopic device in accordance with the present disclosure is constructed to cross-clamp the nerve/ligament bundles and to conduct radiofrequency current through the tissue. The radiofrequency current is applied in a controlled manner to heat the tissue to a temperature that denatures the neurons and impairs the cells ability to transmit sympathetic or parasympathetic signals. In some embodiments, the tissues of the mesenteric and pelvic nerves, the efferent and afferent nerves of the suspensory ligament of the ovary, efferent and afferent nerves of the ovarian ligament, and/or efferent and afferent nerves of the uterosacral ligament are heated to a range of about 45° C. to about 65° C. for a period of about 5 seconds to about 60 seconds.

In another embodiment, an electrosurgical instrument is provided having a pair of opposing jaw members, e.g., a first jaw member and a second, opposing jaw member, having an open and a closed position wherein, in the open position, the suspensory ligament of the ovary may be introduced therebetween and, in the closed position, the jaw members grasp the suspensory ligament. The opposing jaw members are configured to deliver electrosurgical energy to tissue grasped therebetween. An electrode is disposed on a tissue-facing portion of each jaw member. The electrosurgical instrument is introduced into the vicinity of the suspensory ligament of the ovary. The opposing jaw members are positioned in the open position, and at least a portion of the suspensory ligament of the ovary is introduced between the open jaw members. The opposing jaw members are positioned in the closed position to effectively grasp the suspensory ligament of the ovary therebetween. Electrosurgical energy is delivered from the jaw members to the suspensory ligament of the ovary held therebetween. In some embodiments, energy is delivered in a bipolar manner whereby electrosurgical energy flows from the electrode of a first jaw member, through the suspensory ligament of the ovary held therebetween, and to the electrode of the second jaw member.

In some embodiments, the opposing jaw members are configured to maintain a minimum distance therebetween while in the closed position. In some embodiments, at least one of the jaw members may include one or more stop members configured to maintain a minimum gap distance between jaw members while in the closed position. Preferably, the minimum gap distance is within a range of about 0.001" to about 0.006". In some embodiments, the opposing jaw members are configured deliver compressive force within a predetermined range to a suspensory ligament of the ovary grasped therebetween. Preferably, the compressive force delivered by the jaw members is in a range of about 3 kg/cm$^2$ to about 16 kg/cm$^2$. At least one of a power level, a voltage, a current, a frequency, a crest factor, a waveform, or a duty cycle of the electrosurgical energy is controlled and/or monitored to maintain a temperature of the grasped suspensory ligament of the ovary within a range of about 45° C. to about 65° C. In some embodiments, afferent and/or efferent neural activity of the suspensory ligament of the ovary is monitored, and a change in such afferent and/or efferent neural activity is utilized to determine at least one of a power level of electrosurgical energy or a time duration of application of electrosurgical energy. The electrosurgical energy is delivered to suspensory ligament of the ovary for a period of about 5 seconds to about 60 seconds.

In some embodiments, the electrosurgical instrument includes a temperature sensor configured to sense a temperature of tissue grasped between the jaw members.

In another aspect, the electrosurgical instrument is configured to operably couple with an electrosurgical system. The electrosurgical system includes in operative communication at least one of a current sensor, a voltage sensor, a sensor interface unit, a controller, a high voltage power supply, and a user interface. In embodiments, the electrosurgical system includes at least one of a safety unit or a timer unit.

In some embodiments, the electrosurgical system includes a neural interface configured to receive one or more neural monitoring signals from one or more neural monitoring sensors. Prior to treatment, the neural monitoring sensor(s) are positioned at an afferent and/or efferent nerve or nerve bundle corresponding to the suspensory ligament of the ovary. Delivery of electrosurgical energy to suspensory ligament of the ovary may be terminated and/or regulated in response to a signal received from the one or more neural monitoring sensors. In some embodiments, the delivery of electrosurgical energy may be interrupted and/or modulated when a neural signal reached a predetermined value, or falls within a predetermined range. In this manner, clinically sufficient denervation may be achieved while avoiding unnecessary and/or excessive thermal treatment of targeted tissue, e.g., the suspensory ligament of the ovary, ovarian ligament, or uterosacral ligament.

In another embodiment, an electrosurgical instrument is introduced into the vicinity of the ovarian ligament.

In another embodiment, an electrosurgical instrument is introduced into the vicinity of the uterosacral ligament.

The present disclosure describes a surgical instrument for treating tissue that is economical to manufacture and is capable of sealing and cutting relatively large tissue structures. The surgical instrument includes an elongated shaft having a distal portion and a proximal portion coupled to a housing. The elongated shaft defines a longitudinal axis. An inner shaft member extends at least partially through the elongated shaft. The inner shaft member is selectively movable in a longitudinal direction with respect to the elongated shaft. An end effector adapted for treating tissue is supported by the distal portion of the elongated shaft. The end effector includes upper and lower jaw members pivotally coupled to the distal portion of the elongated shaft about a pivot axis. The upper and lower jaw members include a first and second pair of laterally spaced flanges, respectively. The first and second pairs of flanges of the jaw members are arranged in an offset configuration such that one flange of the upper jaw member is positioned on a laterally exterior side of a corresponding flange of the lower jaw member, and the other flange of the upper jaw member is positioned on a laterally interior side of the other flange of the lower jaw member.

Additionally or alternatively, the housing includes a movable actuating mechanism configured to cause longitudinal movement of the inner shaft member relative to the elongated shaft.

Additionally or alternatively, the elongated shaft includes at least one feature formed therein configured to operably engage the movable actuating mechanism.

Additionally or alternatively, the elongated shaft has a generally circular profile joined along two opposing longitudinal edges.

Additionally or alternatively, the upper and lower jaw members are constructed as substantially identical components positioned in a laterally offset manner with respect to one another.

Additionally or alternatively, the pivot axis extends through each of the flanges in a direction substantially transverse to the longitudinal axis.

Additionally or alternatively, the inner shaft member extends through the jaw members on a laterally interior side of each of the flanges.

Additionally or alternatively, the surgical instrument includes a knife selectively movable in a longitudinal direction with respect to the inner shaft member.

Additionally or alternatively, the inner shaft member includes a knife guide disposed on a distal end of the inner shaft member such that the knife is substantially surrounded on four lateral sides.

According to another aspect of the present disclosure, a surgical instrument is provided. The surgical instrument includes an elongated shaft including a distal portion and a proximal portion coupled to a housing. The elongated shaft defines a longitudinal axis. An end effector adapted for treating tissue is supported by the distal portion of the elongated shaft. The end effector includes first and second jaw members pivotally coupled to one another to move between open and closed configurations. Each of the jaw members includes a pair of laterally spaced flanges. Each of the flanges includes a camming surface. A knife extends at least partially through the elongated shaft and is selectively movable in a longitudinal direction between the flanges of the jaw members. A blade of the knife is extendable into a tissue contacting portion of the jaw members. An inner shaft member extends at least partially through the elongated shaft and is selectively movable in a longitudinal direction with respect to the knife and with respect to the elongated shaft. The inner shaft member carries a cam pin positioned to engage the camming surface of each of the flanges to induce the jaw members to move between the open and closed configurations.

Additionally or alternatively, the elongated shaft includes at least one feature defined therein configured to engage a movable actuating mechanism operably associated with the housing.

Additionally or alternatively, the laterally spaced flanges of the jaw members are arranged in a nestled configuration wherein both of the flanges of one of the jaw members are arranged within a laterally interior side of the laterally spaced flanges of the other of the jaw members.

According to another aspect of the present disclosure, a method of manufacturing a surgical device including a housing and an elongated shaft for coupling an end effector with the housing of the surgical device is provided. The method includes the steps of stamping at least one feature into a blank of sheet metal and folding the blank into such that two opposing longitudinal edges of the blank meet at a longitudinal seam to form an elongated shaft. The method also includes the step of operably coupling an end effector to at least one feature formed at a distal portion of the elongated shaft. The method also includes the step of engaging at least one actuating mechanism supported by a housing with at least one feature formed at a proximal portion of the elongated shaft to operably couple the proximal portion of the elongated shaft with the housing. The actuating mechanism is configured to selectively move the end effector between an open position and a closed position.

Additionally or alternatively, the method includes the step of joining the two opposing longitudinal edges along the longitudinal seam.

Additionally or alternatively, the joining step further comprises laser welding the longitudinal seam. The longitudinal seam may be a box joint configuration or a dovetail joint configuration.

Additionally or alternatively, the method includes the step of coupling a drive rod to the at least one actuating mechanism at a proximal end and to the end effector at a distal end. The drive rod may be configured to translate within and relative to the elongated shaft upon movement of the at least one actuation mechanism to effect actuation of the end effector.

Additionally or alternatively, the method includes the step of stamping at least one feature at a distal end of the blank such that a clevis is formed at a distal end of the elongated shaft. The clevis may be configured to support the end effector.

In another aspect, a method for treating premenstrual dysphoric disorder in a mammalian being is disclosed. The method includes inducing neuromodulation of a neural fiber that contributes to ovarian function. In some embodiments, neural fiber that contributes to ovarian function is selected from the group consisting of nerves of the suspensory ligament of the ovary, nerves of the ovarian ligament, nerves of the uterosacral ligament, an inferior mesenteric nerve bundle, and a pelvic nerve bundle.

In some embodiments, inducing neuromodulation of the neural fiber includes delivering electro surgical energy to the neural fiber.

In some embodiments, inducing neuromodulation of the neural fiber includes delivering microwave energy to the neural fiber.

In some embodiments, inducing neuromodulation of the neural fiber includes delivering acoustic energy to the neural fiber.

In some embodiments, delivering acoustic energy to the neural fiber includes delivering high frequency focused ultrasound to the neural fiber.

In some embodiments, inducing neuromodulation of the neural fiber includes increasing the temperature of the neural fiber. In some embodiments, the temperature of the neural fiber is increased to a temperature in a range of about 45° C. to about 65° C.

In some embodiments, inducing neuromodulation of the neural fiber includes monitoring the temperature of the neural fiber.

In some embodiments, inducing neuromodulation of the neural fiber includes monitoring the impedance of the neural fiber.

In some embodiments, inducing neuromodulation of the neural fiber includes delivering energy to the neural fiber. In some embodiments, energy is delivered to the neural fiber for a duration of about 5 seconds to about 60 seconds. In some embodiments, energy delivery to the neural fiber is interrupted based upon a sensed neural activity of the neural fiber decreasing to a predetermined value.

In some embodiments, inducing neuromodulation of the neural fiber includes monitoring neural activity of the neural fiber.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
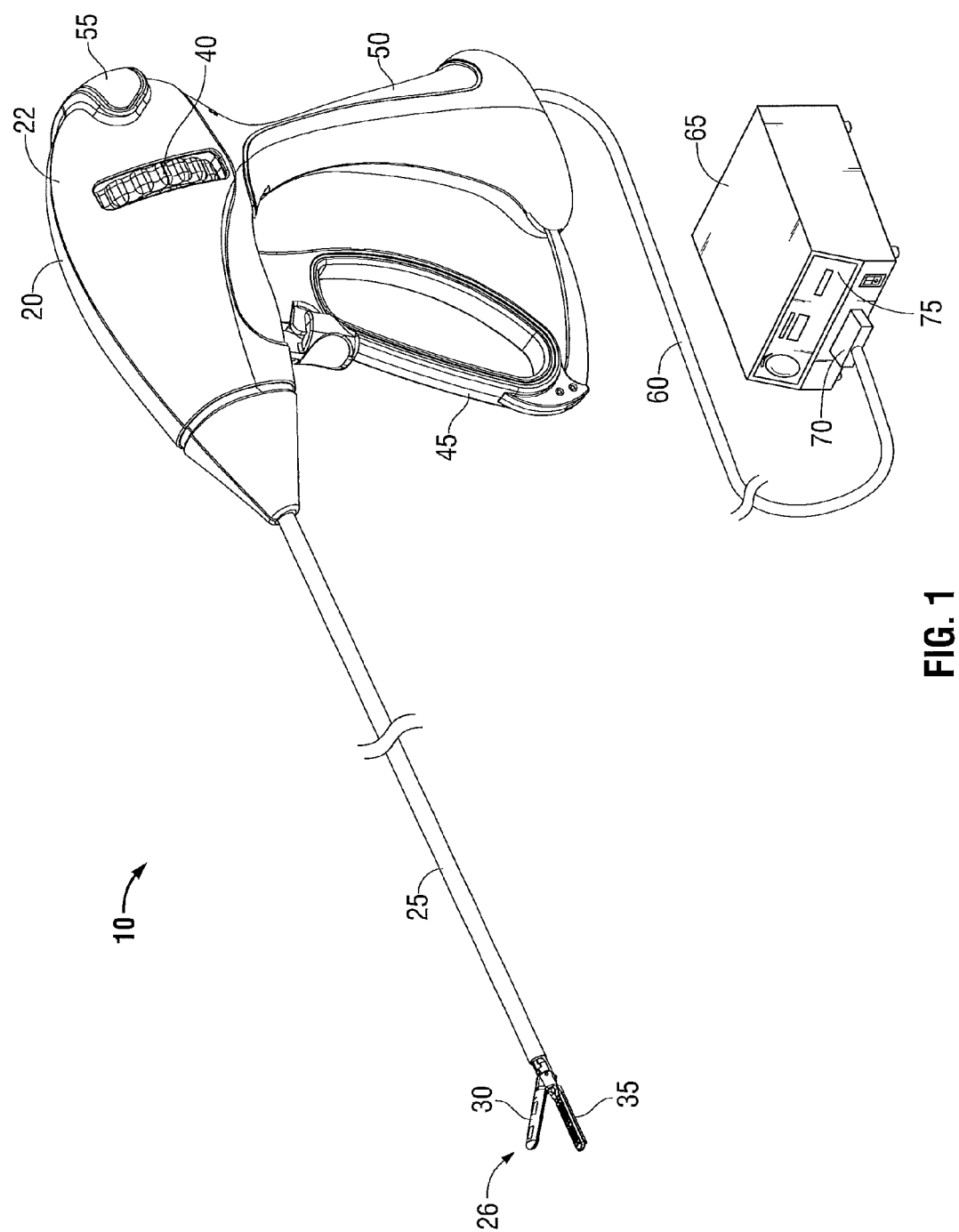
FIG. 1 is a perspective view of an electrosurgical system for uterine denervation in accordance with an embodiment of the present disclosure.

Particular embodiments of the present disclosure will be described hereinbelow with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In the drawings and in the descriptions that follow, the term "proximal," as is traditional, shall refer to the end of the instrument that is closer to the user, while the term "distal" shall refer to the end that is farther from the user. In this description, as well as in the drawings, like-referenced numbers represent elements which may perform the same, similar, or equivalent functions.

With reference to FIG. 1, an embodiment of an electrosurgical system 10 configured to perform a method of denervation of the sympathetic and parasympathetic nerves of the ovaries and/or uterus of a patient 110 in accordance with the present disclosure is presented. The disclosed system and method may be utilized for the treatment of PMDD, and additionally or alternatively, may be utilized for the purpose of contraception by inducing reversible or permanent sterility in patient 110. While a human example is shown in the drawings, it should be understood the present disclosure is directed to the treatment of any mammalian being.

The system 10 includes a denervation instrument 20 that is configured to operably couple with electrosurgical generator 65. To electrically control delivery of electrosurgical energy to jaw members 30, 35, the housing 22 supports a switch 55 thereon, which is operable by the user to initiate and terminate the delivery of electrosurgical energy to jaw members 30, 35. The switch 55 is in electrical communication with a source of electrosurgical energy such as electrosurgical generator 65 or a battery (not shown) supported within the housing 22. The generator 65 may include devices such as the LIGASURE® Vessel Sealing Generator and the Force Triad® Generator as sold by Covidien Energy-based Devices of Boulder, Colo. A cable 60 extends between the housing 22 and the generator 65 and may include a connector 70 thereon such that the instrument 20 may be selectively coupled and decoupled electrically from the generator 65. In some embodiments, denervation instrument 20 may include a vessel sealing instrument, such as, without limitation, an electrosurgical forceps such as that described in U.S. Pat. No. 7,255,697 to Dycus et al.

Instrument 20 includes a housing 22 having a grip 50 extending therefrom and a handle 45 that is movable between a first position whereby handle 45 is positioned in spaced relation apart from grip 50 and a second position whereby handle 45 is positioned in spaced relation closer to grip 50 than in the first position. A shaft 25 extends distally from housing 22 and includes at a distal end 26 thereof opposing jaw members 30, 35. Jaw members 30, 35 are moveable between an open position whereby jaw 30 is positioned in spaced relation apart from jaw 35 and a second position whereby jaw 30 is positioned in spaced relation closer to jaw 35 to grasp tissue therebetween, such as, without limitation, a suspensory ligament of the ovary, a uterosacral ligament, and/or an ovarian ligament.

Instrument 20 may include a rotating control 40 that enables a user to rotate shaft 25 and/or jaw members 30, 35 around a longitudinal axis of the shaft 25 to position jaw members 30, 35 as necessary with respect to the surgical site without necessitating the twisting of housing 22, handle 50, etc. Generator 65 includes a user interface 75 configured to display operational data and provide audible tones to a user, and to accept user inputs.

Figure 2:
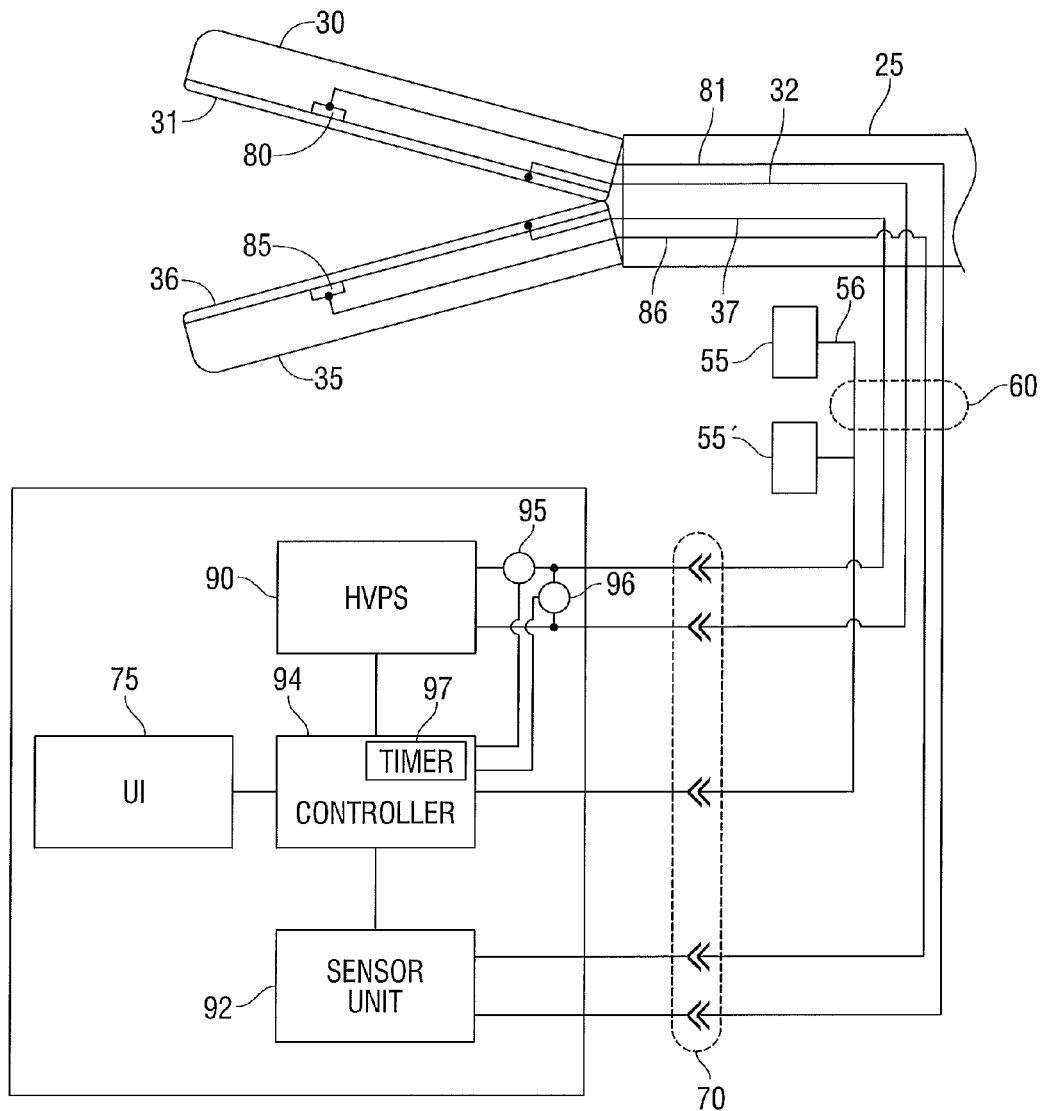
FIG. 2 is a functional diagram of an electrosurgical system for uterine denervation in accordance with an embodiment of the present disclosure.

With reference additionally now to FIG. 2, the opposing jaw members 30, 35 are electrically coupled to cable 60, and thus to the generator 65, via conductors 32, 37 respectively, that extend through the elongated shaft 25 to provide an electrical pathway to a pair of electrically conductive, tissue-engaging sealing plates 31, 36 disposed on the tissue-contacting faces of jaw members 30, 35, respectively. A pair of wire conduits (not explicitly shown) that may be formed from a plastic tube, may be provided to guide conductors 32, 37 from jaw members 30, 35 proximally to the housing 22 and to protect conductors 32, 37 from sharp edges that may form on surrounding components. The sealing plate 31 of jaw member 30 opposes the sealing plate 36 of jaw member 35, and, in some embodiments, the sealing plates 31 and 36 are electrically coupled to opposite terminals, e.g., positive or active (+) and negative or return (−) terminals associated with the generator 65. Thus, bipolar energy may be provided through the sealing plates 31, 36. Alternatively, the sealing plates 31, 36 may be configured for delivering monopolar energy to the tissue. In a monopolar configuration, one or both sealing plates 31, 36 deliver electrosurgical energy from an active terminal, e.g. (+), while a return pad (not explicitly shown) is placed generally on a patient and provides a return path to the opposite terminal, e.g. (−), of the generator 65.

Jaw members 30, 35 include temperature sensors 80, 85, respectively. Temperature sensors 80, 85 are configured to sense a temperature of the corresponding jaw member 30, 35, sealing plate 31, 36, and/or tissue grasped between jaw members 30, 35, e.g., a suspensory ligament of the ovary, a uterosacral ligament, and/or an ovarian ligament. Temperature sensors 80, 85 may include a thermocouple, a thermistor, a forward-biased diode, an infrared radiation temperature sensor, and/or an interferometric temperature sensor. Temperature sensors 80, 85 are operatively coupled to cable 60, and thus to the generator 65, via conductors 81, 86 respectively, that extend through the elongated shaft 25 to provide a communication pathway to generator 65. In some embodiments, conductors 81, 86 may include an electrical conductor (e.g., metallic or carbon-based conductors). In some embodiments, conductors 81, 86 may include an optical conductor (e.g., fiber optic).

In some embodiments, generator 65 includes a number of modules in operable communication, including a high voltage power supply (HVPS) unit 90, a controller unit 94, a sensor unit 92, and a user interface 75. HVPS 90 is configured to selectively deliver electrosurgical energy in response to one or more control signals received from controller unit 94. Controller unit 94 is configured to receive user input signals from switch 55 and user interface 75 and is configured to receive sensor signals from sensor unit 92. Sensor unit 92 is operatively coupled to temperature sensors 85, 86 via conductors 81, 86; controller 94 is operably coupled to switch 55 via conductor 56; and HVPS 90 is operably coupled to sealing plates 31, 36 by conductors 32, 37. Conductors 32, 37, 56, 81, and 86 may be included in cable 60 and detachably coupled to generator 65 via connector 70. Generator 65 includes a current sensor 95 disposed in series with an output of HVPS 90, and a voltage sensor 96 disposed in parallel with an output of HVPS 90, that are in operable communication with controller 94 and which may be utilized by controller 94 to compute tissue impedance during use. Similar generators are described in commonly-owned U.S. Pat. Nos. 7,927,328 and 8,211,099, the entirety of each of which are incorporated by reference herein.

In some embodiments, controller 94 may be configured to control the RF output to follow a denervation treatment profile. The treatment profile defines a treatment cycle in which a treatment time, a target temperature, and/or a target impedance are specified to be attained in order to effectuate denervation. Upon receipt of an activation signal from switch 55, controller 94 issues a control signal to HVPS 90, which, in turn, causes HVPS 90 to initiate delivery of electrosurgical energy to sealing plates 31, 36. Concurrently upon issuance of the control signal, controller 94 starts a treatment timer 97 that is configured to terminate the delivery of electrosurgical energy upon expiration of a predetermined treatment interval. The treatment interval may be in the range from about 5 seconds to about 60 seconds, and may be entered directly by the surgeon via user interface 75, and/or may be determined in accordance with one or more preset treatment profiles.

In some embodiments, the treatment timer 97 begins timing when a temperature sensed by temperature sensor 80 and/or 85 reaches a predetermined value and/or falls within a predetermined range. In these embodiments, controller 94 ensures that denervation is successfully achieved by ensuring proper heating of the neural fibers during the treatment cycle, and that only the period of time during which targeted tissue is maintained within the defined range of treatment temperature is considered for timing purposes.

In some embodiments, controller 94 is configured to terminate the delivery of electrosurgical energy delivered by HVPS 90 when a temperature sensed by temperature sensor 80 and/or 85 exceeds a predetermined value, falls within a predetermined range, or falls outside a predetermined range.

Options for processing by controller 94 of activation signals received from switch 55 may be predetermined, or, in some embodiments, may be selected by a user via user interface 75. For example, without limitation, a first actuation of switch 55 may initiate a treatment profile. Upon release of switch 55, the treatment cycle continues until it concludes normally (e.g., the competition of a profile-defined treatment time, the attainment of a profile-defined tissue temperature, and/or the attainment of a profile-defined tissue impedance), or, until switch 55 is actuated a subsequent time. In this mode, switch 55 acts as a toggle, e.g., a first push activates the treatment cycle, and a second push terminates the cycle. In another mode, switch 55 must be continuously actuated (e.g., continuously pressed) during a treatment cycle. In this mode, the treatment cycle will conclude normally provided switch 55 remains actuated through the cycle, or, the treatment cycle will terminate upon release of switch 55. In some embodiments, a second switch 55' may be provided that is configured to terminate a treatment cycle upon actuation thereof. In these embodiments, switch 55 begins the treatment cycle, and the switch 55' terminates the treatment cycle early, if necessary.

Figure 3:
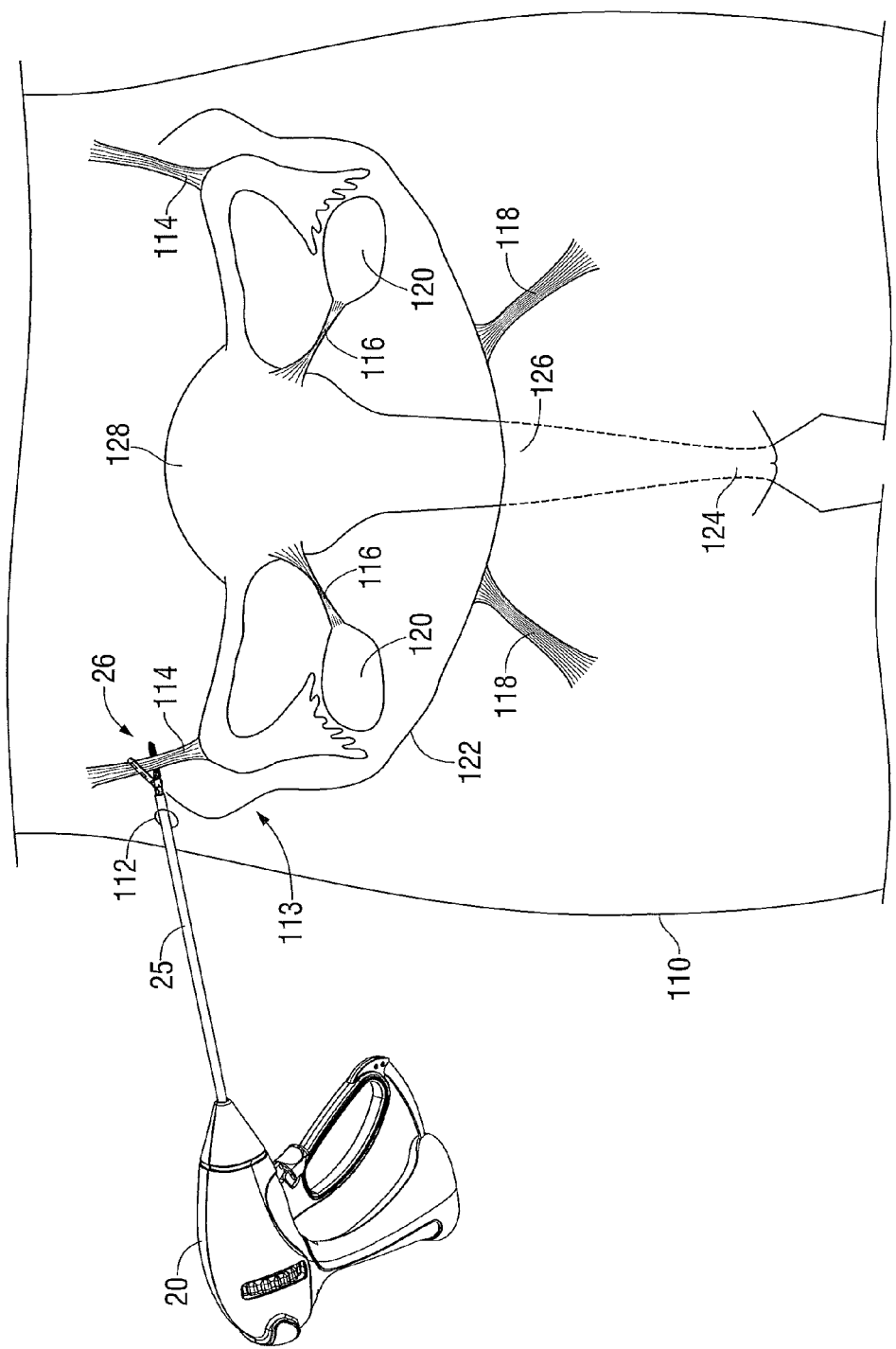
FIG. 3 is a perspective view of an endoscopic electrosurgical device performing a method of denervation of the suspensory ligament of the ovary with in accordance with an embodiment of the present disclosure.
Figure 4:
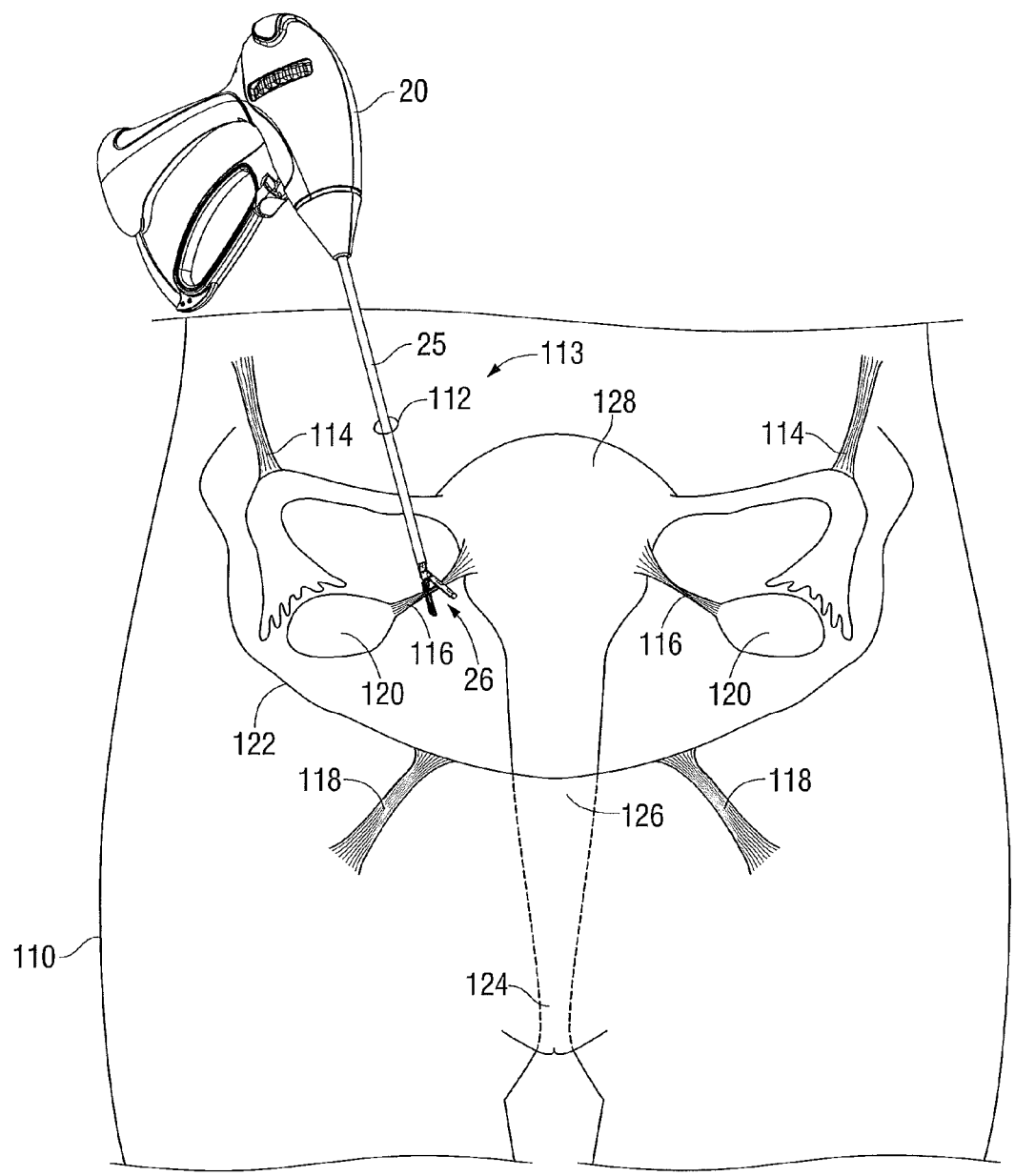
FIG. 4 is a perspective view of an endoscopic electrosurgical device performing a method of denervation of the ovarian ligament in accordance with an embodiment of the present disclosure.
Figure 5:
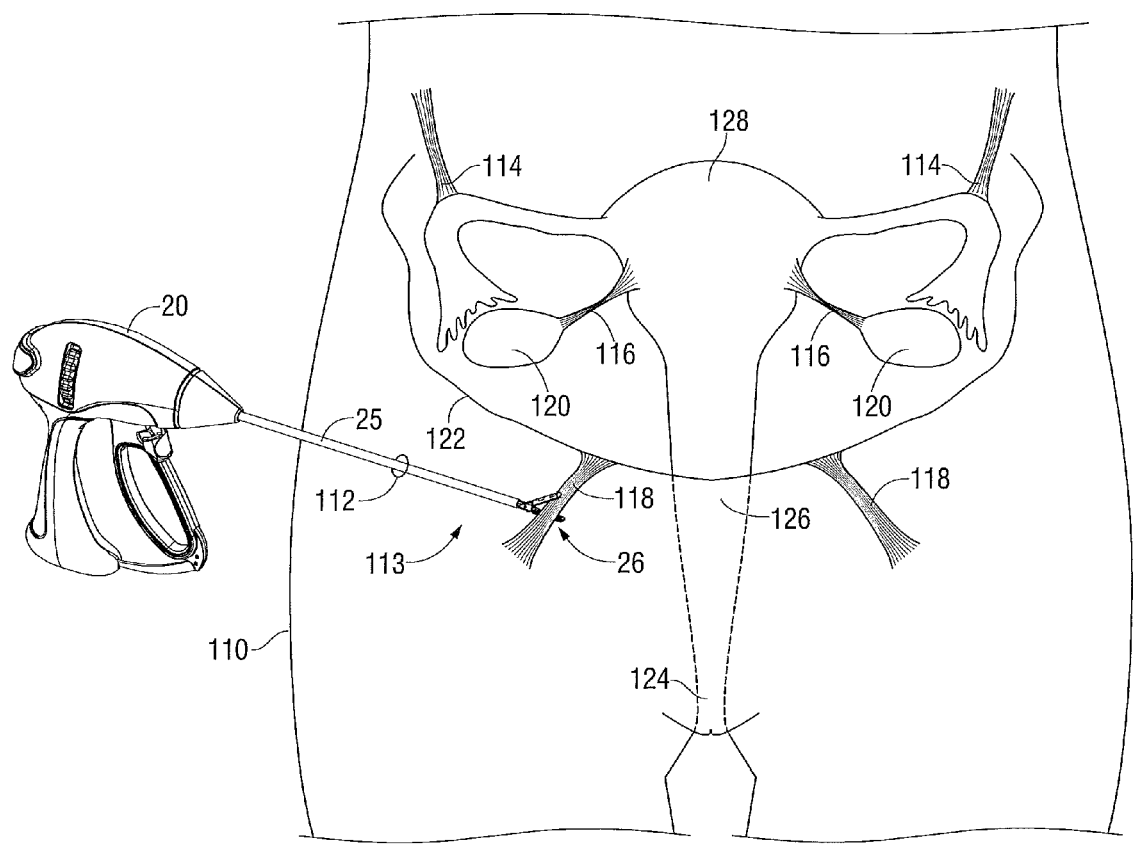
FIG. 5 is a perspective view of an endoscopic electrosurgical device performing a method of denervation of the uterosacral ligament in accordance with an embodiment of the present disclosure.

Turning to FIGS. 3, 4, and 5, embodiments of systems and methods for treating PMDD in accordance with the present disclosure are presented. An endoscopic device is introduced to the pelvic space and located such that radiofrequency energy is conducted through the tissue of the inferior mesenteric or pelvic nerves. In FIG. 3, denervation (e.g., neuromodulation) of the suspensory ligament of the ovary 114 is illustrated; in FIG. 4, denervation of the ovarian ligament 116 is illustrated; and in FIG. 5, denervation of the uterosacral ligament 118 is shown.

It is to be understood that alternative systems and methods of performing denervation of the suspensory ligament of the ovary 114, ovarian ligament 116, and/or uterosacral ligament 118 are contemplated, including thermally-induced denervation (heating and/or cooling), denervation by application of infrared energy, denervation by application of microwave energy (e.g., radiofrequency energy in the range of about 915 Mhz to about 2.54 Ghz), denervation by application of acoustic energy (e.g., ultrasound, high-intensity focused ultrasound), and/or denervation by application of electric fields. While the methods and procedures are described illustratively as treating tissue unilaterally, it is to be understood that bilateral treatment of the suspensory ligament of the ovary 114, ovarian ligament 116, and/or uterosacral ligament 118 may be performed.

Using a standard interventional approach, an incision 112 is made on an abdominal wall 113 of a female patient 110. The shaft 25 of instrument is introduced into the abdominal cavity and the distal end 26 of the shaft is positioned in the vicinity of the targeted tissue, e.g., suspensory ligament of the ovary 114, ovarian ligament 116, and/or uterosacral ligament 118. Jaw members 30, 35 are moved to an open configuration and positioned such that targeted tissue is located therebetween. Jaw members 30, 35 are moved into a closed position thereby grasping the suspensory ligament of the ovary 114, ovarian ligament 116, and/or uterosacral ligament 118 between jaw members 30, 35. Switch 55 is actuated to initiate a treatment cycle, whereby generator 65 is activated and begins delivery of electrosurgical energy to sealing plates 31, 36. Energy is, in turn, delivered to the suspensory ligament of the ovary 114, ovarian ligament 116, and/or uterosacral ligament 118, and particularly, to the portion of the targeted tissue held between jaw members 30, 35. The temperature of the grasped tissue, which includes the targeted afferent and/or efferent neural fibers (not explicitly shown), is raised to range of 45° C. to 65° C. for a period of about 5 seconds to about 60 seconds. Temperature sensors 80, 85 provide feedback to generator 65 which may modulate any of output power, output current, output voltage, duty cycle, and crest factor of the delivered electrosurgical energy to maintain the temperature of the targeted tissue within the desired range. The described procedure may have advantages, for example, by enabling the treatment of PMDD by neuromodulating the efferent and afferent nerve bundles of the suspensory ligament of the ovary 114, ovarian ligament 116, and/or uterosacral ligament 118, while leaving the underlying tissue bundle, e.g., nerve(s) and supportive ligament(s) structurally intact.

Upon completion of the treatment cycle, generator 65 may signal the surgeon by providing audible, visual, and/or tactile feedback to indicate the cycle is complete. Jaw members 30, 35 are opened to release the treated tissue, and the instrument 20 with withdrawn from patient 100.

In some embodiments, an intravaginal, intracervical, intrauteral, or intrarectal approach may be utilized, e.g., shaft 25 is delivered to the surgical site though the vagina 124, via the cervix 126, via the uterus 128, and/or via the rectum (not explicitly shown).

It will be understood that various modifications may be made to the embodiments disclosed herein. Further variations of the above-disclosed and other features and functions, or alternatives thereof, may be desirably combined into many other different systems, instruments and applications. Various presently unforeseen or unanticipated alternatives, modifications, variations or improvements therein may be subsequently made by those skilled in the art, which are also intended to be encompassed by the following claims.

What is claimed is:

1. A method for treating premenstrual dysphoric disorder in a mammalian being, the method comprising:
   inducing denervation of a neural fiber that contributes to ovarian function by delivering energy to the neural fiber through jaw members grasping tissue including the neural fiber, wherein the grasped tissue between the jaw members includes a tissue bundle underlying the neural fiber and the tissue bundle disposed between the jaw members remains structurally intact;

terminating the delivery of the energy, the tissue bundle underlying the neural fiber and the tissue disposed between the jaw members at the termination being structurally intact; and opening the jaw members to release the structurally intact tissue.

2. The method in accordance with claim 1, wherein the neural fiber that contributes to ovarian function is selected from the group consisting of nerves of the suspensory ligament of the ovary, nerves of the ovarian ligament, nerves of the uterosacral ligament, an inferior mesenteric nerve bundle, and a pelvic nerve bundle.

3. The method in accordance with claim 1, wherein the energy in the inducing denervation of the neural fiber comprises electrosurgical energy.

4. The method in accordance with claim 1, wherein the energy in the inducing denervation of the neural fiber comprises microwave energy.

5. The method in accordance with claim 1, wherein the energy in the inducing denervation of the neural fiber comprises acoustic energy.

6. The method in accordance with claim 5, wherein the acoustic energy comprises high frequency focused ultrasound to the neural fiber.

7. The method in accordance with claim 1, wherein inducing denervation of the neural fiber comprises increasing a temperature of the neural fiber.

8. The method in accordance with claim 7, wherein the temperature of the neural fiber is increased to a temperature in a range of about 45° C. to about 65° C.

9. The method in accordance with claim 1, wherein inducing denervation of the neural fiber comprises monitoring a temperature of the neural fiber.

10. The method in accordance with claim 1, wherein inducing denervation of the neural fiber comprises monitoring an impedance of the neural fiber.

11. The method in accordance with claim 1, wherein the energy is delivered to the neural fiber for a duration of about 5 seconds to about 60 seconds.

12. The method in accordance with claim 1, wherein delivery of the energy to the neural fiber is interrupted based upon a sensed neural activity of the neural fiber decreasing to a predetermined value.

13. The method in accordance with claim 1, wherein inducing denervation of the neural fiber comprises monitoring neural activity of the neural fiber.

14. A method for treating premenstrual dysphoric disorder in a mammalian being, the method comprising:
grasping between jaw members of a surgical instrument tissue including a neural fiber that contributes to ovarian function and a tissue bundle underlying the neural fiber;
supplying energy to the jaw members grasping the tissue including the neural fiber to thereby deliver the energy to the neural fiber through the jaw members to induce denervation of the neural fiber, wherein the tissue bundle underlying the neural fiber remains structurally intact;
terminating the delivery of the energy, the tissue bundle underlying the neural fiber and the tissue disposed between the jaw members at the termination being structurally intact; and
opening the jaw members to release the structurally intact tissue.

* * * * *